(12) United States Patent
Soon et al.

(10) Patent No.: US 7,087,289 B2
(45) Date of Patent: Aug. 8, 2006

(54) APERTURED ELASTIC MEMBER

(75) Inventors: See Aun Soon, Eschborn (DE); Jorg Muller, Karben (DE)

(73) Assignee: The Procter & Gamble Company, Cincinnati, OH (US)

( * ) Notice: Subject to any disclaimer, the term of this patent is extended or adjusted under 35 U.S.C. 154(b) by 324 days.

(21) Appl. No.: 10/148,759

(22) PCT Filed: Dec. 1, 2000

(86) PCT No.: PCT/US00/32872

§ 371 (c)(1),
(2), (4) Date: May 31, 2002

(87) PCT Pub. No.: WO01/39712

PCT Pub. Date: Jun. 7, 2001

(65) Prior Publication Data

US 2002/0182371 A1    Dec. 5, 2002

(30) Foreign Application Priority Data

Dec. 1, 1999    (EP) .................................. 99123829

(51) Int. Cl.
*B32B 3/10*    (2006.01)
*A61F 5/44*    (2006.01)

(52) U.S. Cl. ...................... 428/137; 604/336
(58) Field of Classification Search ............... 428/137; 604/336
See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 3,911,173 A | 10/1975 | Sprague, Jr. |
| 4,107,364 A | 8/1978 | Sisson |
| 4,166,464 A * | 9/1979 | Korpman .................... 604/366 |
| 4,209,563 A | 6/1980 | Sisson |
| 4,381,781 A | 5/1983 | Sciaraffa et al. |
| 4,515,595 A | 5/1985 | Kievit et al. |
| 4,525,407 A | 6/1985 | Ness |
| 4,573,986 A | 3/1986 | Minetola et al. |
| 4,573,991 A | 3/1986 | Pieniak et al. |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,710,189 A | 12/1987 | Lash |
| 4,785,996 A | 11/1988 | Ziecker et al. |
| 4,795,454 A | 1/1989 | Dragoo |
| 4,808,178 A | 2/1989 | Aziz et al. |
| 4,816,025 A | 3/1989 | Foreman |

(Continued)

FOREIGN PATENT DOCUMENTS

EP    0 409 315 B1    1/1991

(Continued)

*Primary Examiner*—Harold Pyon
*Assistant Examiner*—Patricia L Nordmeyer
(74) *Attorney, Agent, or Firm*—George H. Leal; Thibault Fayette; Matthew P. Fitzpatrick

(57) ABSTRACT

An apertured elastic member having a first direction, a second direction perpendicular to the first direction and a substantially constant thickness dimension. The apertures are aligned in a pattern of rows substantially parallel to the first direction. A nonapertured region extends uninterrupted between adjacent rows of apertures parallel to the first direction. The member has a plurality of repeating units, each having substantially the same amount of material everywhere along the repeating unit in a direction parallel to the second direction.

19 Claims, 5 Drawing Sheets

U.S. PATENT DOCUMENTS

| | | | |
|---|---|---|---|
| 4,834,735 A | 5/1989 | Alemany et al. | |
| 4,834,741 A | 5/1989 | Sabee | |
| 4,842,666 A | 6/1989 | Werenicz | |
| 4,846,815 A | 7/1989 | Scripps | |
| 4,857,067 A | 8/1989 | Wood et al. | |
| 4,888,231 A | 12/1989 | Angstadt | |
| 4,894,060 A | 1/1990 | Nestegard | |
| 4,909,803 A | 3/1990 | Aziz et al. | |
| 4,938,753 A | 7/1990 | Van Gompel et al. | |
| 4,946,527 A | 8/1990 | Battrell | |
| 4,963,140 A | 10/1990 | Robertson et al. | |
| 4,988,344 A | 1/1991 | Reising et al. | |
| 4,988,345 A | 1/1991 | Reising | |
| 5,026,364 A | 6/1991 | Robertson | |
| 5,137,537 A | 8/1992 | Herron et al. | |
| 5,143,679 A | 9/1992 | Weber et al. | |
| 5,147,345 A | 9/1992 | Young et al. | |
| 5,151,092 A | 9/1992 | Buell et al. | |
| 5,156,793 A | 10/1992 | Buell et al. | |
| 5,167,897 A | 12/1992 | Weber et al. | |
| 5,221,274 A | 6/1993 | Buell et al. | |
| 5,336,554 A * | 8/1994 | Knight | 428/137 |
| 5,342,338 A | 8/1994 | Roe | |
| 5,376,198 A * | 12/1994 | Fahrenkrug et al. | 156/164 |
| 5,554,143 A | 9/1996 | Roe et al. | |
| 5,554,144 A | 9/1996 | Roe et al. | |
| 5,554,145 A | 9/1996 | Roe et al. | |
| 5,556,394 A | 9/1996 | Roe et al. | |
| 5,569,232 A | 10/1996 | Roe et al. | |
| 5,571,096 A | 11/1996 | Dobrin et al. | |
| 5,607,760 A | 3/1997 | Roe | |
| 5,609,587 A | 3/1997 | Roe | |
| 5,635,191 A | 6/1997 | Roe et al. | |
| 5,643,588 A | 7/1997 | Roe et al. | |
| 5,669,897 A | 9/1997 | Lavon et al. | |
| 5,865,823 A | 2/1999 | Curro | |
| 6,106,925 A * | 8/2000 | Palumbo | 428/137 |

FOREIGN PATENT DOCUMENTS

| WO | WO 95/24173 | 9/1995 |
|---|---|---|

\* cited by examiner

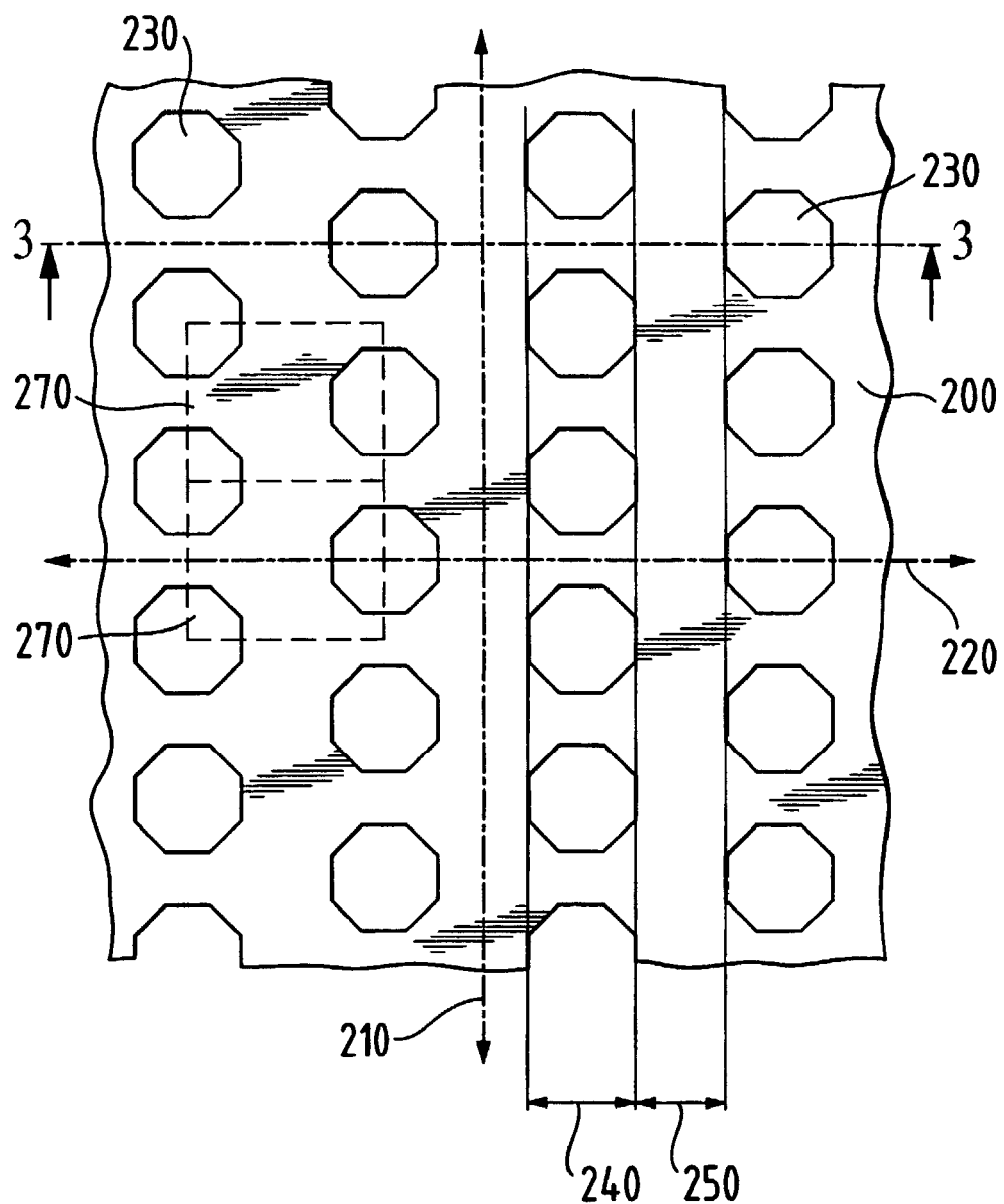
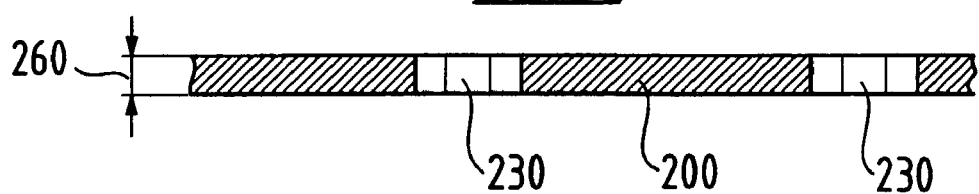

APERTURED ELASTIC MEMBER

FIELD OF THE INVENTION

The present invention relates to absorbent articles such as diapers, incontinent briefs, training pants, and the like, and more particularly to absorbent articles having at least one apertured elastic member.

BACKGROUND OF THE INVENTION

The major function of absorbent articles such as disposable diapers and adult incontinent briefs is to absorb and contain body exudates. Such articles are thus intended to prevent body exudates from soiling, wetting, or otherwise contaminating clothing or other articles, such as bedding, that come in contact with the wearer. Absorbent articles thus function both to contain the discharged materials and to isolate these materials form the body of the wearer and from the wearer's garments and bed clothing. However, absorbent articles have a tendency to sag or gap away form and to slide/slip down on the body of the wearer during wear. This sagging/gapping and sliding/slipping is caused by the relative motions of the wearer as the wearer breathes, moves and changes positions, by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer in the waist regions and the regions of the absorbent article.

Disposable absorbent articles have been marketed which include one or more elastic or stretch members to provide improved fit about the waist and legs of the wearer. An example of a disposable diaper with an elastomeric waist feature which has achieved wide acceptance and commercial success is disclosed in U.S. Pat. No. 4,515,595 issued to Kievit and Osterhage on May 7, 1985. Elastic waist features will typically comprise an elasticized waistband consisting of an elastomeric member contractibly affixed between the topsheet and the backsheet. The elasticized waistband is, thus, designed to expand and contract with the wearer's motions and to maintain, the fit of the absorbent article about the waist of the wearer during use. Disposable absorbent articles having elastic leg features are also known to the art. For example, U.S. Pat. No. 3,860,003, entitled "Contractable Side Portions For Disposable Diaper" issued to Buell on Jan. 14, 1975, describes an absorbent article having an elasticized leg cuff which has achieved wide acceptance and commercial success.

Methods for stretching an elastic member are described in U.S. Pat. No. 4,107,364, issued to Sisson on Aug. 15, 1978, U.S. Pat. No. 4,209,563 issued to Sisson on Jun. 24, 1980, U.S. Pat. No. 4,525,407 issued to Ness on Jun. 25, 1985, U.S. Pat. No. 4,834,741 issued to Sabee on May 30, 1989, European Patent Publication 409,315 published Jan. 23, 1991.

Still other methods are described in U.S. Pat. Nos. 5,167,897, 5,156,793, and U.S. patent application Ser. No. 07/662543, each filed Feb. 28, 1991 and assigned to The Procter & Gamble company. These patents describe making an elasticized laminate by mechanically stretching making a zero-strain stretch laminate web to impart the elasticity hereto in the direction of stretching, at least up to the point of initial stretching.

Conventionally, the elastic feature of an absorbent article consists of a laminate web of at least one elongatable, non-elastic nonwoven layer and at least one elastic member with both layers in their relaxed state. The laminate web is elasticized by mechanically stretching at least portions of the laminate web along its width to impart elasticity thereto in the direction of stretching, at least up to the point of initial stretching. The elastomeric web may fist undergo a "cut and slip" operation prior to activation by mechanical stretching, so that it has the required dimensions as the elastic feature of the absorbent circle. Such operations are described in U.S. Pat. Nos. 5,167,897 and 5,156,793 and additionally in U.S. Pat. No. 5,143,679.

In numerous instances the elastic member is a solid, non-breathable member which can cause undue build-up of moisture against the skin of the wearer if the article worn for an extended period of time. In order to solve this problem, apertured elastic members have been used to provide both elasticity and breathability. An example of such a design is shown in U.S. Pat. No. 4,573,991. The elastic member of U.S. Pat. No. 4,573,991 comprises longitudinal and transverse interconnected elastic strands, commonly referred to as elastomeric scrim. One of the drawbacks associated with elastomeric scrim is that the elongation forces are not uniform in all directions. Furthermore, the scrim has a very uneven surface as the portion of the scrim where the strands overlap are bumpy and can lead to skin irritations.

It is an object to solve the problems presented by the use of scrims by providing an apertured elastomeric member which has substantially uniform elongation forces and has a very even or uniform thickness dimension throughout.

SUMMARY OF THE INVENTION

The present invention is directed to an apertured elastic member having a first direction, a second direction perpendicular to the first direction and a substantially constant thickness dimension. The apertures are aligned in a pattern of rows parallel extending substantially parallel to the first direction. A nonapertured region extends uninterrupted between adjacent rows of apertures parallel to the first direction. The elastic member has a plurality of repeating units, each having substantially the same amount of material everywhere along the repeating unit in a direction parallel to the second direction.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements.

FIG. 2 is a plan view illustration of an elastic member of the present invention.

FIG. 3 is a cross-sectional illustration of the member of FIG. 2 taken along section line 3—3 of FIG. 2.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner.

Figure 1:
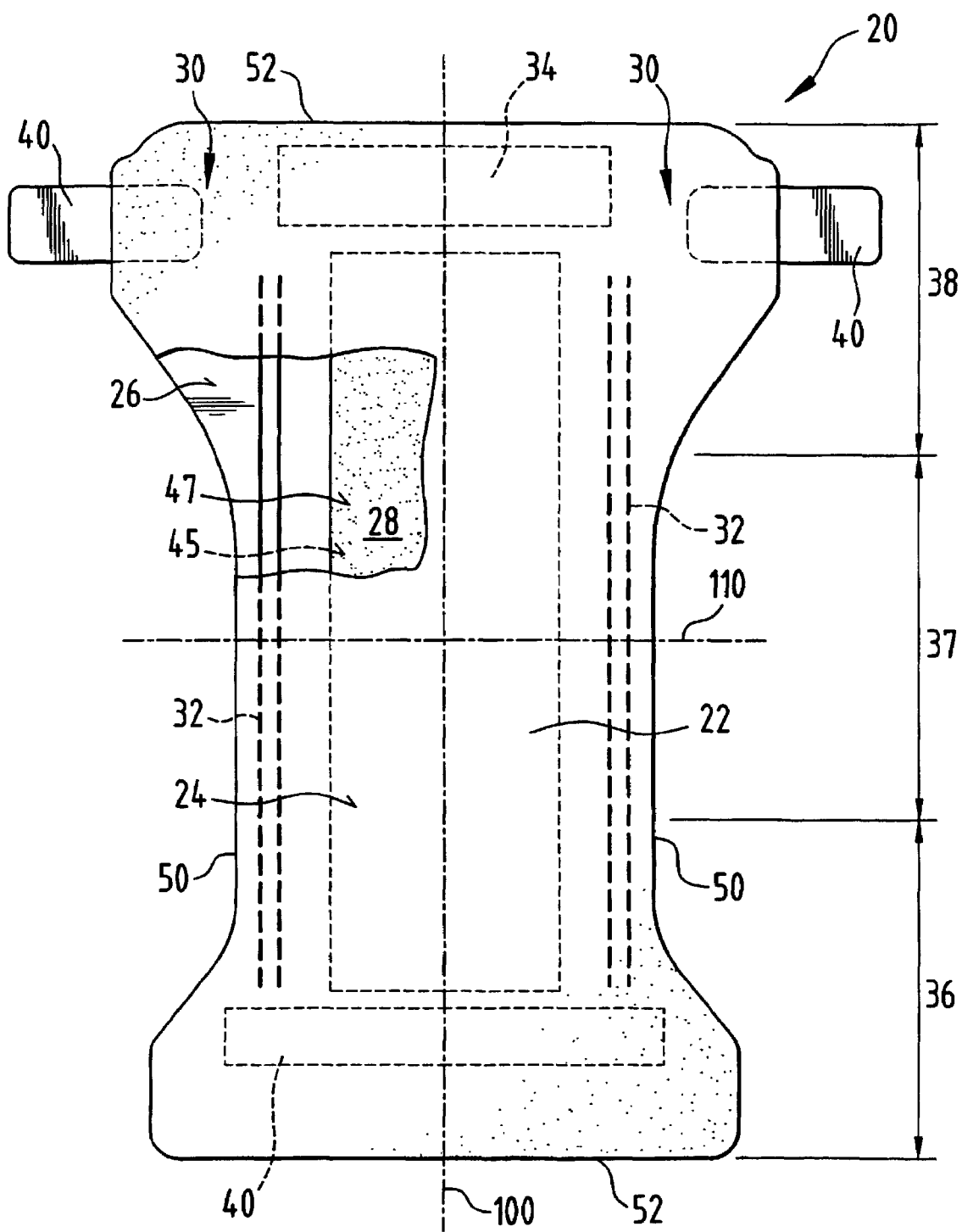
FIG. 1 is a plan view of illustration of a prior art disposable diaper.

A unitary disposable absorbent article, diaper 20, is shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, and the like.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the chassis 22 may be assembled in a variety of well known configurations, suitable diaper configurations are described generally in U.S. Pat. Nos. 3,860,003; 5,151,092; 5,221,274; 5,569,232; 5,554,144; 5,554,143; 5,554,145; and 5,556,394.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173; 4,785,996; and 4,842,666. Adhesives which have been found to be satisfactory are manufactured by H. B. Fuller Company of St. Paul, Minn. and marketed as HL-1258. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; woven or nonwoven webs of natural fibers (e.g., wood or cotton fibers), synthetic fibers (e.g., polyester or polypropylene fibers), or a combination of natural and synthetic fibers or apertured woven or nonwoven webs. If the absorbent assemblies include fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. Nos. 4,988,344 and 4,988,345.

Any portion of the topsheet 24 may be coated with a lotion as is known in the art. Examples of suitable lotions include those described in U.S. Pat. Nos. 5,607,760; 5,609,587; 5,635,191; and 5,643,588. The topsheet may also include or be treated with antibacterial agents, some examples of which are disclosed in PCT Publication No. WO 95/24173. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent assemblies are described in U.S. Pat. Nos. 4,610,678; 4,673,402; 4,834,735,; 4,888,231; 5,137,537; and 5,147,345; 5,342,338.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge of the absorbent core 28 and generally forms at least a portion of the end edge of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. Nos. 4,515,595; 4,710,189; 5,151,092; and 5,221,274. Other suitable waist configurations may include waistcap features such as those described in U.S. Pat. Nos. 5,026,364 and 4,816,025. All of the above mentioned references are incorporated herein by reference.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. Nos. 4,857,067; 4,381,781; 4,938,753; 5,151,092; 5,221,274; 5,669,897; each of which is incorporated herein by reference.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No.

3,860,003 describes a disposable diaper which provides a contractible leg opening having a side flap and one or more elastic members to provide an elasticized leg cuff (a gasketing cuff). U.S. Pat. No. Nos. 4,808,178 and 4,909,803, respectively, describe disposable diapers having "stand-up" elasticized flaps (barrier cuffs) which improve the containment of the leg regions. U.S. Pat. Nos. 4,695,278 and 4,795,454, respectively, describe disposable diapers having dual cuffs, including gasketing cuffs and barrier cuffs.

The diaper 20 may also include a fastening system 40. The fastening system 40 preferably maintains the first waist region 36 and the second waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. Nos. 3,848,594; 4,662,875 B1; 4,846,815; 4,894,060; 4,946, 527; 5,151,092; and 5, 221,274. The fastening system may also provide a means for holding the article in a disposal configuration as disclosed in U.S. Pat. No. 4,963,140. Each of these patents is incorporated herein by reference.

Referring now to FIG. 2 there is shown a plan view illustration of an elastic member 200 of the present invention. Elastic member 200 may be used as the elastic member in the elastic waist feature 34, the side panels 30, the tape tabs of the fastening system 40, the leg cuffs 32 and the topsheet 24 of the diaper 20 illustrated in FIG. 1. Of course these are merely representative of the vast number of potential uses for the elastic member 200 of the present invention and by no means are meant to be limiting.

The apertured elastic member 200 may be any stretchable or elastomeric material. (As used herein, the terms "stretchable" refers to materials that are extensible when forces are applied to the material, and offer some resistance to extension. The term "elastomeric" refers to materials that extend in at least one direction when a force is applied to the material, and return to approximately their original dimensions after the force is released.) Suitable materials for the apertured elastic member 200 include but are not limited to elastomeric foams, "live" synthetic or natural rubber, elastomeric films (including heat-shrinkable elastomeric films, Kraton based elastomeric films, metallocene catalyzed polyethylene films, vacuum formed elastic films), or the like. The apertured elastic member 200 may comprise a single layer or multiple layers.

Elastic member 200 has a first direction 210 and a second direction 220 which extends perpendicular to the first direction 210. The elastic member 200 comprises a plurality of apertures 230 which are aligned in a pattern of rows 240. Rows 240 extend in a direction substantially parallel to the first direction 210. In special cases an angle of up to 15 degrees may be desired for smaller elastic members that only contain a small number of holes (generally less than 50 in one row). The angle should be chosen such that the nonapertured bands (or regions) still have a finite width. While the apertures shown in FIG. 2 have an octagonal shape other aperture shapes are also within the scope of the present invention. Other suitable aperture shapes include but are not limited to circular, triangular, oval, square, hexagonal, elliptical, and rectangular. In addition the size and number of the apertures may also be selected to provide the desired properties, such as open area or breathability. The elastic member may have an open area from 5% to 80%, more preferably, the elastic member may have an open area from 10% to 50%. Of course, the exact open area may selected as desired.

Separating adjacent rows 240 are nonapertured regions 250 which extend uninterrupted substantially parallel to the first direction 210. The dimensions of rows 240 and regions or rows 250 may be of the same or different dimensions. The range of dimensions being determined by the intended use of the member 200. The member 200 is intended to be stretched in a direction parallel to the first direction 210 which is also parallel to the direction in which the continuous unapertured regions 250 extend.

Referring now to FIG. 3 there is shown a cross-sectional illustration of the apertured elastic member 200 taken along section line 3—3 of FIG. 2. As can be seen in FIG. 3 the member 200 has a substantially constant thickness dimension 260 throughout. Substantially constant thickness dimension includes small variations due to machine tolerances during manufacture and process variability causing standard variations of less than 15% of the members averaged thickness dimension.

Referring again to FIG. 2, the member 200 includes a plurality of repeating units 270. Several repeating units are depicted in FIG. 2. Everywhere along each repeating unit 270 in a direction parallel to the second direction 220, i.e., the direction perpendicular to the direction of stretch, the unit 270 has substantially the same amount of material or a substantially constant cross-sectional area.

Figure 4:
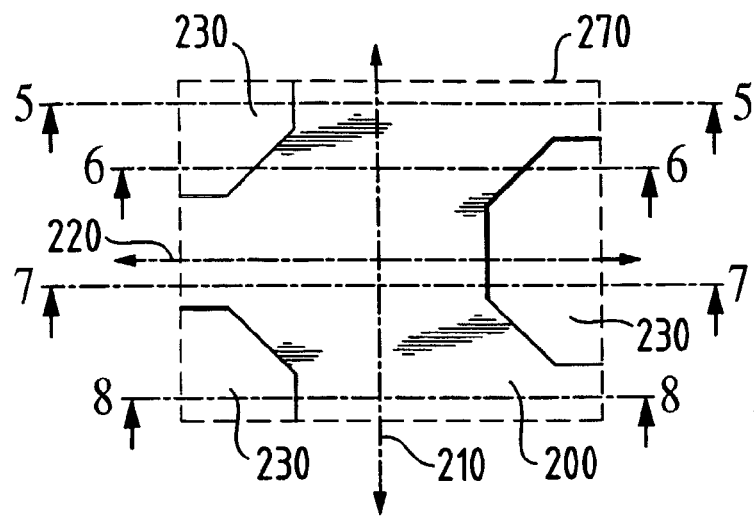
FIG. 4 is an enlarged plan view illustration of a single repeating unit of the elastic member of FIG. 2.
Figure 5:
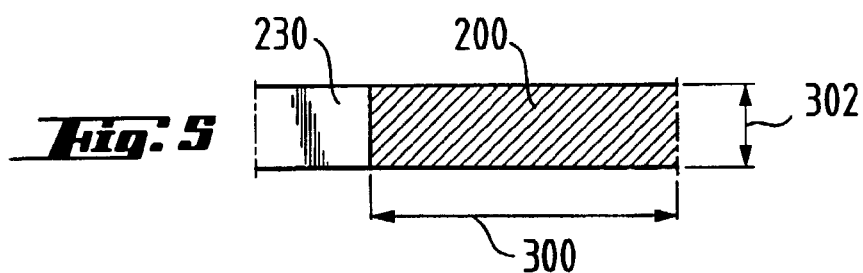
FIGS. 5–8 are cross-sectional illustrations taken along section lines 5—5, 6—6, 7—7, and 8—8 of FIG. 4.
Figure 6:
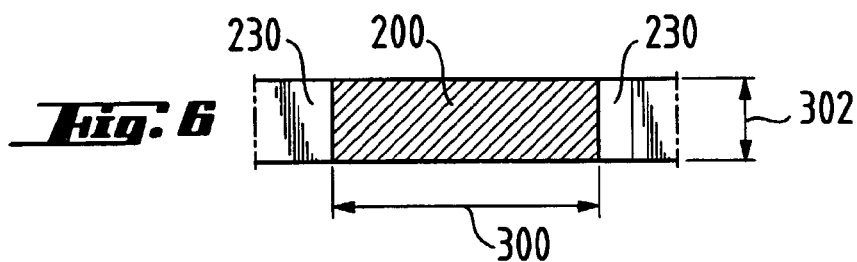
Figure 7:
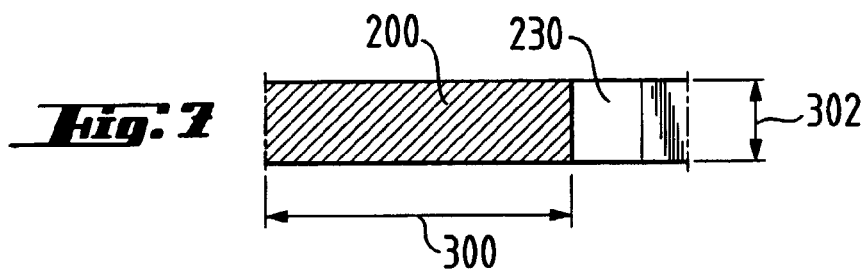
Figure 8:
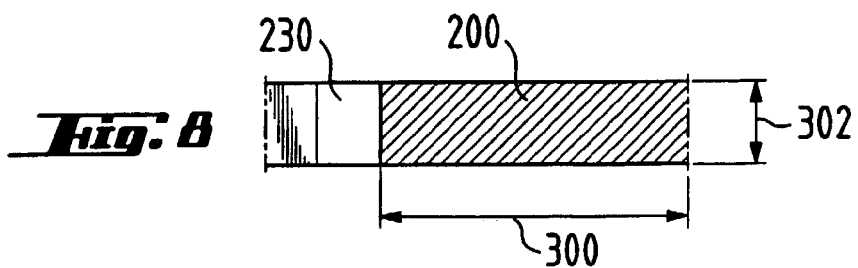

Referring now to FIG. 4 there is an enlarged plan view of a single repeating unit 270 which comprises portions of apertures 230. First direction 210 and second direction 220 are both indicated for reference. FIGS. 5–8 are cross-sectional views taken along repeating unit 270 to illustrate the constant cross-sectional area of the unit 270 in a direction parallel to the second direction 220.

As can be seen in FIGS. 5–8, the unit 270 has an amount of material or cross-sectional area equal to dimension 300 multiplied by dimension 302. Dimension 302 represents the thickness of the member 200 which is substantially constant and dimension 300 represents the length of the material taken along a particular reference line.

Figure 9:
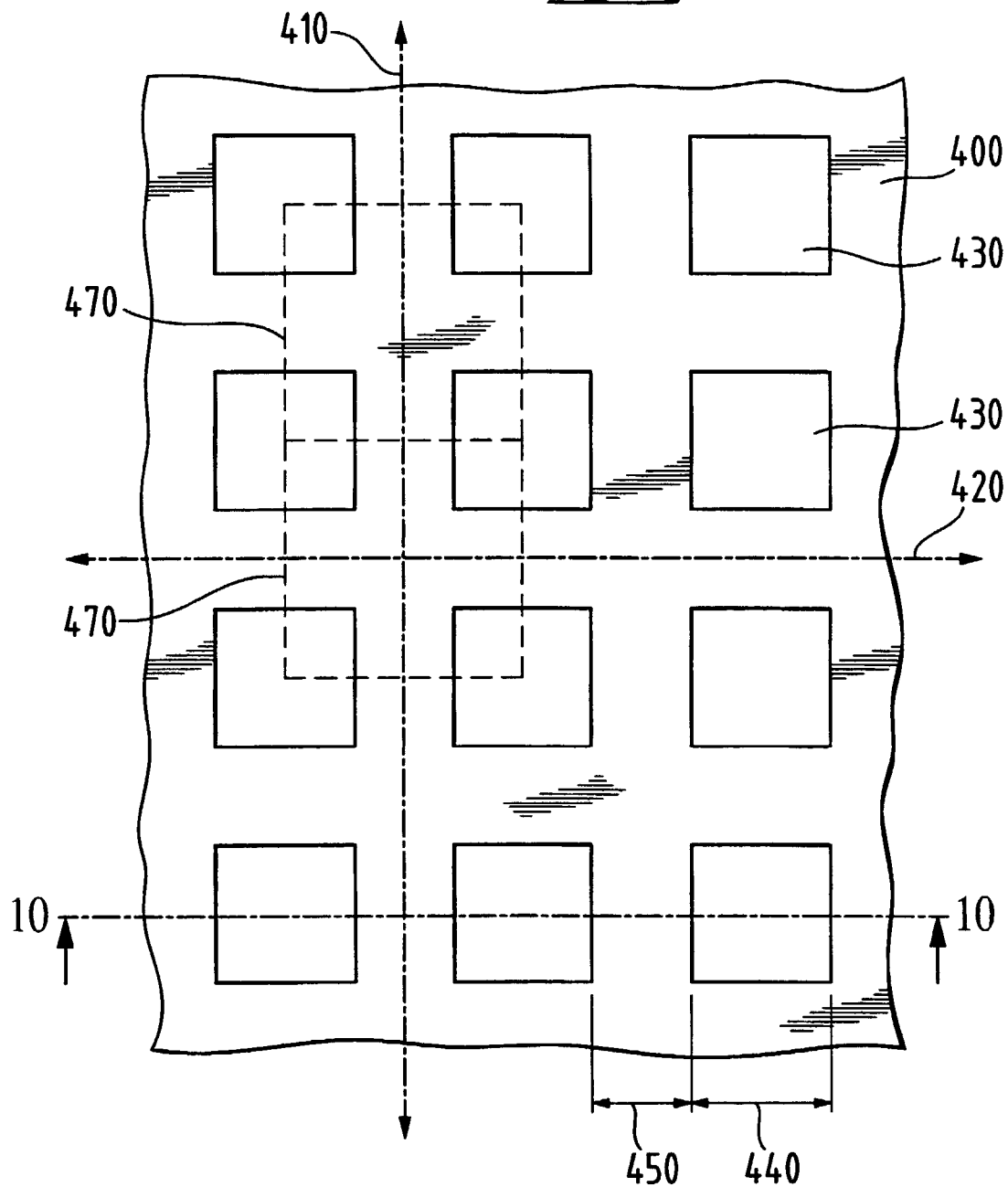
FIG. 9 is plan view illustration of an elastic member not within the scope of the present invention.

To understand the importance of the aperture pattern depicted in FIGS. 2–8, it is helpful to look at an elastic member having an aperture pattern not within the scope of the present invention. Referring now to FIG. 9, there is illustrated an elastic member 400 not within the scope of the present invention. Elastic member 400 has a first direction 410 and a second direction 420 which is perpendicular to the first direction 410. The member 400 has a plurality of apertures 430 which are aligned in a pattern of rows 440. Rows 440 extend in a direction parallel to the first direction 410. Separating adjacent rows 440 are nonapertured regions 450 which extend uninterrupted parallel to the first direction 410. The member 400 is intended to be stretched in a direction parallel to the first direction 410 which is also parallel to the continuous unapertured regions 450. Since the pattern of apertures in member 400 is the same in both directions 410 and 420, the member could also be stretched in direction 420. However, for discussion purposes, the direction of stretch will be parallel to direction 410.

Figure 10:
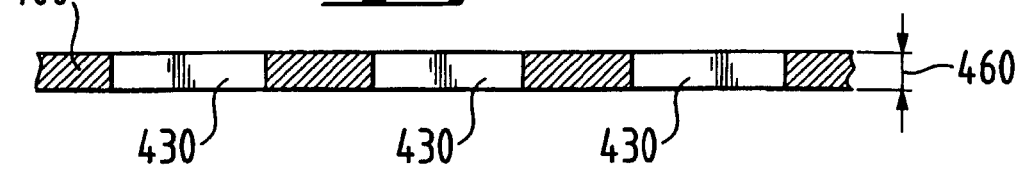
FIG. 10 is a cross-sectional illustration taken along section line 10—10 of FIG. 9.

Referring now to FIG. 10 there is shown a cross-sectional illustration of the member 400 taken along section line 10—10 of FIG. 9. As can be seen in FIG. 10 the member 400 has a substantially constant thickness dimension 460 throughout.

The member 400 includes a plurality of repeating unit 470. Several repeating units 470 are depicted in FIG. 9.

Unlike units 270 of member 200, units 470 of member 400 do not have substantially the same amount of material of substantially constant cross-sectional area everywhere along the unit in a direction parallel to the second direction 420. The amount of material, in the claimed invention, along the repeating unit, in a direction parallel to the second direction, preferably varies by less than 10%. Even more preferably, the amount of material along the repeating unit, in a direction parallel to the second direction, varies by less than 2%.

Figure 11:
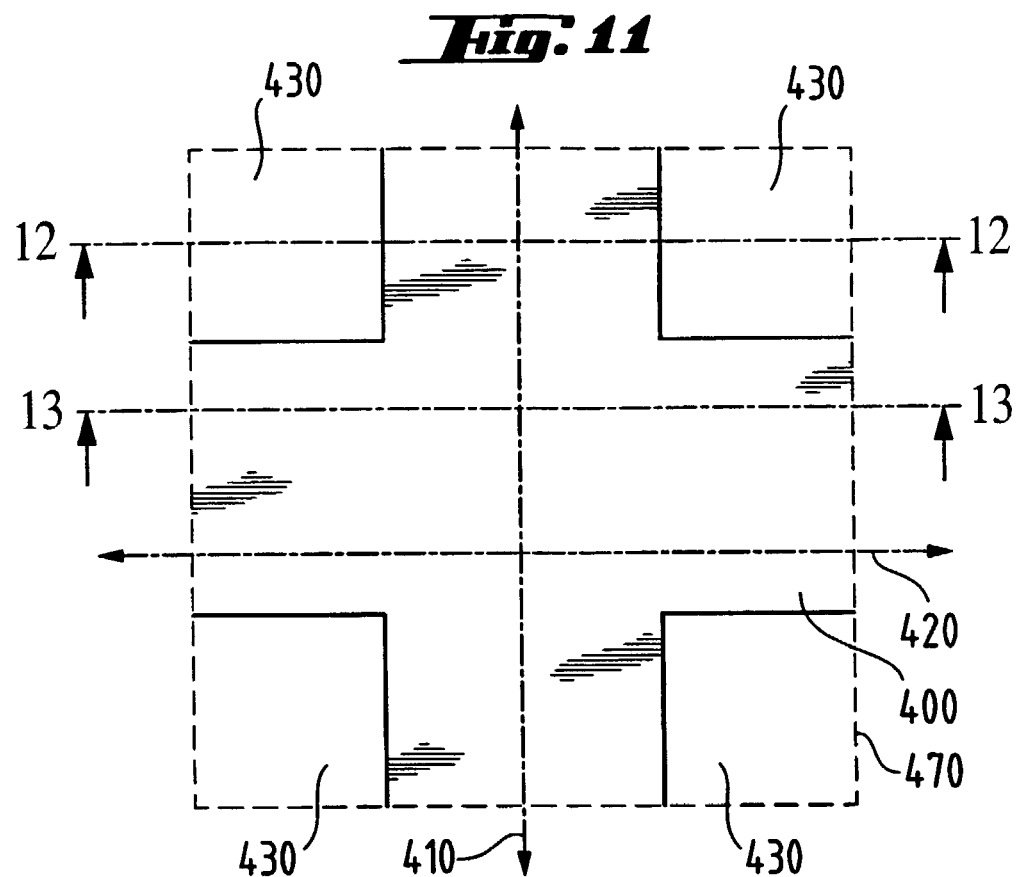
FIG. 11 is an enlarged plan view illustration of a single repeating unit of the elastic member of FIG. 9.
Figure 12:
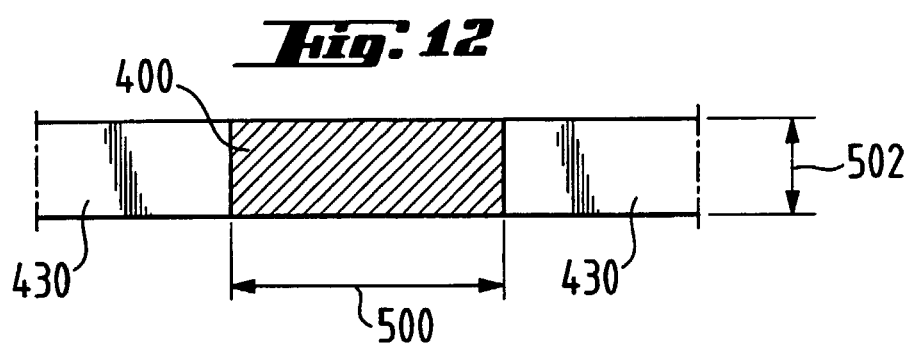
FIGS. 12–13 are cross-sectional illustrations taken along section lines 12—12 and 13—13 of FIG. 11.
Figure 13:
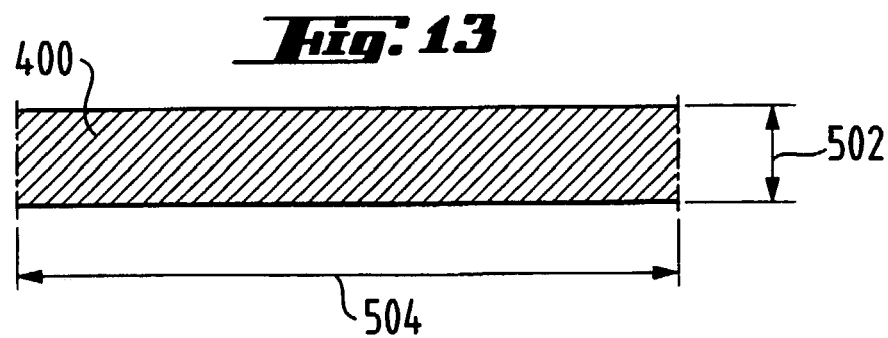

Referring now to FIG. 11 there is an enlarged plan view of a single unit 470 which comprises portions of apertures 430. First direction 410 and second direction 420 are both indicated for reference. FIGS. 12–13 are cross-sectional views taken along repeating unit 470 to illustrate the lack of constant cross-sectional area of the unit 470 in a direction parallel to the second direction 420.

As can be seen in FIG. 12, the unit 470 has an amount of material or cross-sectional area equal to dimension 500 multiplied by dimension 502. As can be seen in FIG. 13, the unit 470 has an amount of material or cross-sectional area equal to dimension 504 multiplied by dimension 502. The cross-sectional area of the unit in FIG. 13 is much larger than the cross-sectional area of the unit in FIG. 12.

The lack of substantially constant cross-sectional area of the unit creates weak regions which are subjected to higher strain than the other regions of the unit during stress. One problem associated with this is an increased risk of the member tearing. Another problem is the non uniformity and overall lower elasticity of the member since the elastic properties generally suffer at higher elongations. The member of the present invention, as shown in FIGS. 2–8, will not posses any weak regions thus avoiding the problems of prior art apertured elastic members.

Any suitable technique for forming apertures may be used to form the apertured elastic member of the present invention. After extrusion, the member may be apertured via a knife and anvil, a punch or vacuum aperturing. If a conventional anvil and knife, punch or vacuum aperturing technique is used, the portions of the member which are cut to form the apertures may be collected and fed back into the extruder such that no material is wasted. Alternatively, the elastic member may be extruded directly onto a forming screen or mold to produced the desired pattern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apertured elastic member having a first direction and a second direction perpendicular to said first direction, said apertured elastic member having a plurality of apertures aligned in a pattern of rows substantially parallel to said first direction, and said apertured elastic member having a substantially constant thickness dimension, the apertured elastic member comprising:
   a plurality of repeating units, wherein a repeating unit comprises a portion of a first aperture from a first row and a portion of a second aperture from a second row, wherein the second row is adjacent to the first row, and a nonapertured region extending between adjacent rows of apertures, and wherein the nonapertured region of the repeating unit has substantially the same cross sectional area everywhere along the repeating unit in a plane that is parallel to the second direction.

2. The elastic member of claim 1 wherein the amount of material everywhere along the repeating unit, in a direction parallel to the second direction, varies by less than 2%.

3. The elastic member of claim 1 wherein the amount of material everywhere along the repeating unit, in a direction parallel to the second direction, varies by less than 10%.

4. The elastic member of claim 1 wherein said elastic member has an open area ranging from 5% to 80%.

5. The elastic member of claim 1 wherein said elastic member has an open area ranging from 10% to 50%.

6. The elastic member of claim 1 wherein said apertures have a shape selected from the group of circular, triangular, oval, square, hexagonal, octagonal, elliptical, and rectangular.

7. The elastic member of claim 1 wherein said elastic member forms part of a disposable absorbent article.

8. The elastic member of claim 7 wherein said elastic member forms an elastic waist feature in the disposable absorbent article.

9. The elastic member of claim 7 wherein said elastic member forms an elastic side panel in the disposable absorbent article.

10. The elastic member of claim 7 wherein said elastic member forms an elastic leg cuff in the disposable absorbent article.

11. The elastic member of claim 7 wherein said elastic member forms a tape tab in a fastening system in the disposable absorbent article.

12. The elastic member of claim 7 wherein said elastic member forms a topsheet in the disposable absorbent article.

13. The apertured elastic member of claim 1, wherein said elastic member has a standard variation of the thickness dimension that is less than 15% of the avenge thickness of the elastic member.

14. An apertured elastic member having a first direction and a second direction perpendicular to said first direction, said apertured elastic member having a plurality of apertures aligned in a pattern of rows substantially parallel to said first direction, and said apertured elastic member having a substantially constant thickness dimension, the apertured elastic member comprising:
   a plurality of repeating units, wherein a repeating unit comprises a portion of a first aperture front a first row, a portion of a second aperture from a second row, a portion of an aperture adjacent to the first aperture or adjacent to the second aperture, wherein the second row is adjacent to the first row, and a nonapertured region extending between adjacent rows of apertures, and wherein the nonapertured region of the repeating unit has substantially the same cross sectional area everywhere along the repeating unit in a plane that is parallel to the second direction.

15. An apertured elastic member having a first direction and a second direction perpendicular to said first direction, said apertured elastic member having a plurality of apertures aligned in a pattern of rows substantially parallel to said first direction, and said apertured elastic member having a substantially constant thickness dimension, the apertured elastic member comprising:
   a plurality of consecutive repeating units, wherein a repeating unit comprises a portion of a first aperture from a first row, a portion of a second aperture from a second row, and a nonapertured region extending between adjacent rows of apertures, wherein the first row is adjacent to the second row, and wherein the nonapertured region of the repeating unit has substantially the same cross sectional area everywhere along the repeating unit in a plane that is parallel to the second direction.

16. The elastic member of claim 15 wherein said elastic member forms an elastic waist feature in the disposable absorbent article.

17. The elastic member of claim 15 wherein said elastic member forms an elastic side panel in the disposable absorbent article.

18. The elastic member of claim 15 wherein said elastic member forms an elastic leg cuff in the disposable absorbent article.

19. The elastic member of claim 15 wherein said elastic member forms a tape tab in a fastening system in the disposable absorbent article.

* * * * *

UNITED STATES PATENT AND TRADEMARK OFFICE
CERTIFICATE OF CORRECTION

PATENT NO.         : 7,087,289 B2                                              Page 1 of 1
APPLICATION NO. : 10/148759
DATED              : August 8, 2006
INVENTOR(S)        : See Aun Soon et al.

It is certified that error appears in the above-identified patent and that said Letters Patent is hereby corrected as shown below:

Column 1
Line 44, delete "maintain," and insert --maintain--.
Column 8
Line 66, delete "unit" and insert --units--.
Column 10
Line 33, delete "avenge" and insert --average--.
Column 10
Line 43, delete "front" and insert --from--.

Signed and Sealed this

Twenty-fourth Day of July, 2007

JON W. DUDAS
*Director of the United States Patent and Trademark Office*